US012623054B2

(12) United States Patent
Zeis

(10) Patent No.: US 12,623,054 B2
(45) Date of Patent: May 12, 2026

(54) HANDLE ASSEMBLY INCLUDING A SMART CATHETER RING CONNECTOR

(71) Applicant: FREUDENBERG MEDICAL, LLC, Beverly, MA (US)

(72) Inventor: Timothy S. Zeis, Charlestown, IN (US)

(73) Assignee: FREUDENBERG MEDICAL, LLC

( * ) Notice: Subject to any disclaimer, the term of this patent is extended or adjusted under 35 U.S.C. 154(b) by 832 days.

(21) Appl. No.: 18/072,746

(22) Filed: Dec. 1, 2022

(65) Prior Publication Data

US 2024/0181211 A1     Jun. 6, 2024

(51) Int. Cl.
*A61M 25/00*         (2006.01)

(52) U.S. Cl.
CPC .... *A61M 25/0097* (2013.01); *A61M 25/0014* (2013.01); *A61M 25/003* (2013.01)

(58) Field of Classification Search
CPC .............. A61M 25/014; A61M 25/003; A61M 25/0136; A61M 25/0158; A61M 25/0097
See application file for complete search history.

(56) References Cited

U.S. PATENT DOCUMENTS 9,510,895 B2 * 12/2016 Houser .......... A61B 17/320092
9,999,762 B2 * 6/2018 Omar-Pasha ........ A61N 1/0551

10,014,607 B1    7/2018  Govari et al.
2009/0306655 A1 * 12/2009  Stangenes ......... A61M 25/0069
                                                                       606/41
2019/0321019 A1 * 10/2019  Novell .............. A61M 25/0102
2020/0121284 A1    4/2020  Schaer et al.
2020/0360083 A1   11/2020  Kelly et al.
2022/0000538 A1    1/2022  Netzel
2022/0280749 A1 *  9/2022  Fargahi ............. A61M 25/0097

FOREIGN PATENT DOCUMENTS

EP          2635205 B1      2/2018

* cited by examiner

*Primary Examiner* — Bhisma Mehta
*Assistant Examiner* — Marissa Taylor
(74) *Attorney, Agent, or Firm* — Dickinson Wright PLLC

(57) ABSTRACT

A handle assembly for a smart catheter includes a housing extending along an axis from a proximal end to a distal end. A smart catheter extends through the housing and along the axis from a receiving end to a distal tip that extends outwardly from and terminates in spaced relationship with the distal end of the housing. The smart catheter includes an outer catheter surface extending annularly about the axis between the receiving end and the distal tip. At least one circuit is disposed along said outer catheter surface and extends between said receiving end and said distal tip. A ring connector is co-axially aligned with said smart catheter and disposed in radially surrounding relationship with a portion of the outer catheter surface to dispose the ring connector in electrical communication with the circuit.

20 Claims, 8 Drawing Sheets

HANDLE ASSEMBLY INCLUDING A SMART CATHETER RING CONNECTOR

BACKGROUND OF THE INVENTION

1. Field of the Invention

The present disclosure relates generally to medical devices and procedures. In particular, the present disclosure relates to a handle assembly for supporting and controlling a steerable catheter.

2. Description of the Prior Art

This section provides background information related to the present disclosure which is not necessarily prior art.

A catheter is a medical instrument for use in accessing an interior of a patient's body with a distal tip during a medical procedure. The catheter can include at least one working component, such as a fluid channel, a working channel, and/or an electronics cable, which extend along the catheter and terminate at or adjacent the distal tip. There is a growing trend in the industry to also integrate circuits into the catheter shaft, thereby providing intelligence to the catheter (i.e., a "smart catheter").

The current state of the art for connectorizing to the circuits in the smart catheter typically involves running a plurality of wires through the smart catheter and out a proximal end, at which point the plurality of wires need to be cut to length, jacket stripped, ends pre-tinned, and then connected via solder or laser welding to electrical contact pads or wires in an umbilical cable disposed inside the handle assembly. However, this is a time consuming and costly manufacturing process, as a result of the multiple cutting, soldering, and/or welding manufacturing processes. Additionally, the resultant handle assembly lacks robustness due to the small, fragile wires which are required to establish an electrical connection to the circuits in the smart catheter. Accordingly, there remains a continuing need for improved ways of establishing an electrical connection with a circuit of the smart catheter during assembly of the handle assembly.

SUMMARY OF THE INVENTION

This section provides a general summary of the disclosure and is not intended to be a comprehensive disclosure of its full scope, aspects, objectives, and/or all of its features.

The subject invention is directed to a handle assembly for a smart catheter that includes a housing extending along an axis from a proximal end to a distal end. A smart catheter extends through the housing and along the axis from a receiving end to a distal tip that extends outwardly from and terminates in spaced relationship with the distal end of the housing. The smart catheter includes an outer catheter surface extending annularly about the axis between the receiving end and the distal tip. At least one circuit is disposed along the outer catheter surface and extends between the receiving end and the distal tip. A ring connector is co-axially aligned with the smart catheter and is disposed in radially surrounding relationship with a portion of the outer catheter surface to dispose the ring connector in electrical communication with the circuit.

The subject invention is also directed to a method of assembling a handle assembly for a smart catheter. The method includes providing a housing extending along an axis from a proximal end to a distal end, and disposing a ring connector within the housing and in axially aligned relationship with the axis. The assembly method proceeds by inserting a smart catheter having an outer catheter surface including at least one circuit into the housing, and then passing the smart catheter through the ring connector to dispose the ring connector and the smart catheter in co-axially aligned relationship. In this position, the ring connector is disposed in radially surrounding relationship with a portion of the outer catheter surface to dispose the ring connector in electrical communication with the at least one circuit.

The handle assembly and method of assembling same in accordance with the subject invention simplifies the process of establishing an electrical connection with the at least one circuit of the smart catheter by eliminating the small, fragile wires and associated soldering and/or welding processes required by the prior art handle assemblies to establish an electrical connection with the circuit(s) of the smart catheter. Put another way, in this simpler manufacturing design, the ring connector functions as a female connector component and the circuit arranged on the outer catheter surface functions as the male connector component to establish a solderless electrical connection between the ring connector and the smart catheter. Thus, the resultant handle assembly is not only more cost effective and easier to assemble due to the solderless design, but the ring connector also makes the overall handle assembly more robust due to reduced likelihood of connector breakage.

Further advantages will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments, and are not all possible implementations and thus are not intended to limit the scope of the present disclosure.

DESCRIPTION OF THE ENABLING EMBODIMENTS

Example embodiments will now be described more fully with reference to the accompanying drawings. The example embodiments are provided so that this disclosure will be thorough and fully convey the scope to those skilled in the art. Numerous specific details are set forth such as examples of specific components, devices, mechanisms, assemblies, and methods to provide a thorough understanding of various embodiments of the present disclosure. It will be apparent to those skilled in the art that specific details need not be employed, that example embodiments may be embodied in many different forms, and that neither should be construed to limit the scope of the disclosure. With this in mind, the present disclosure is directed to a handle assembly 10 including a ring connector 12 for quickly and easily establishing an electrical connection with a smart catheter 14 during assembly and use of the handle assembly 10.

Figure 3:
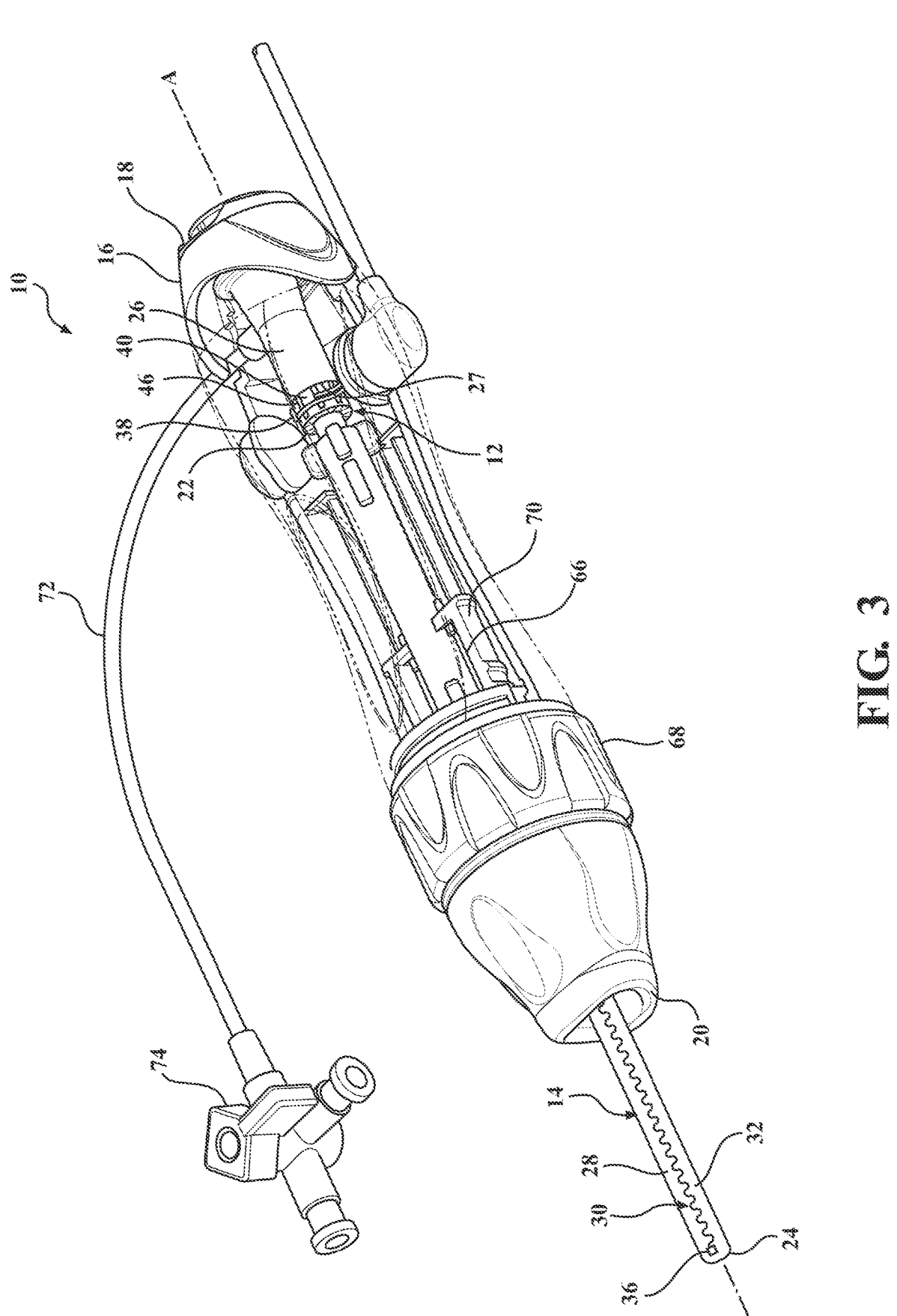
FIG. 3 is a perspective view of a handle assembly constructed in accordance with a first aspect and illustrating a portion of the housing in phantom lines to illustrate the ring connector disposed adjacent a valve assembly at a proximal end of the housing.
Figure 6:
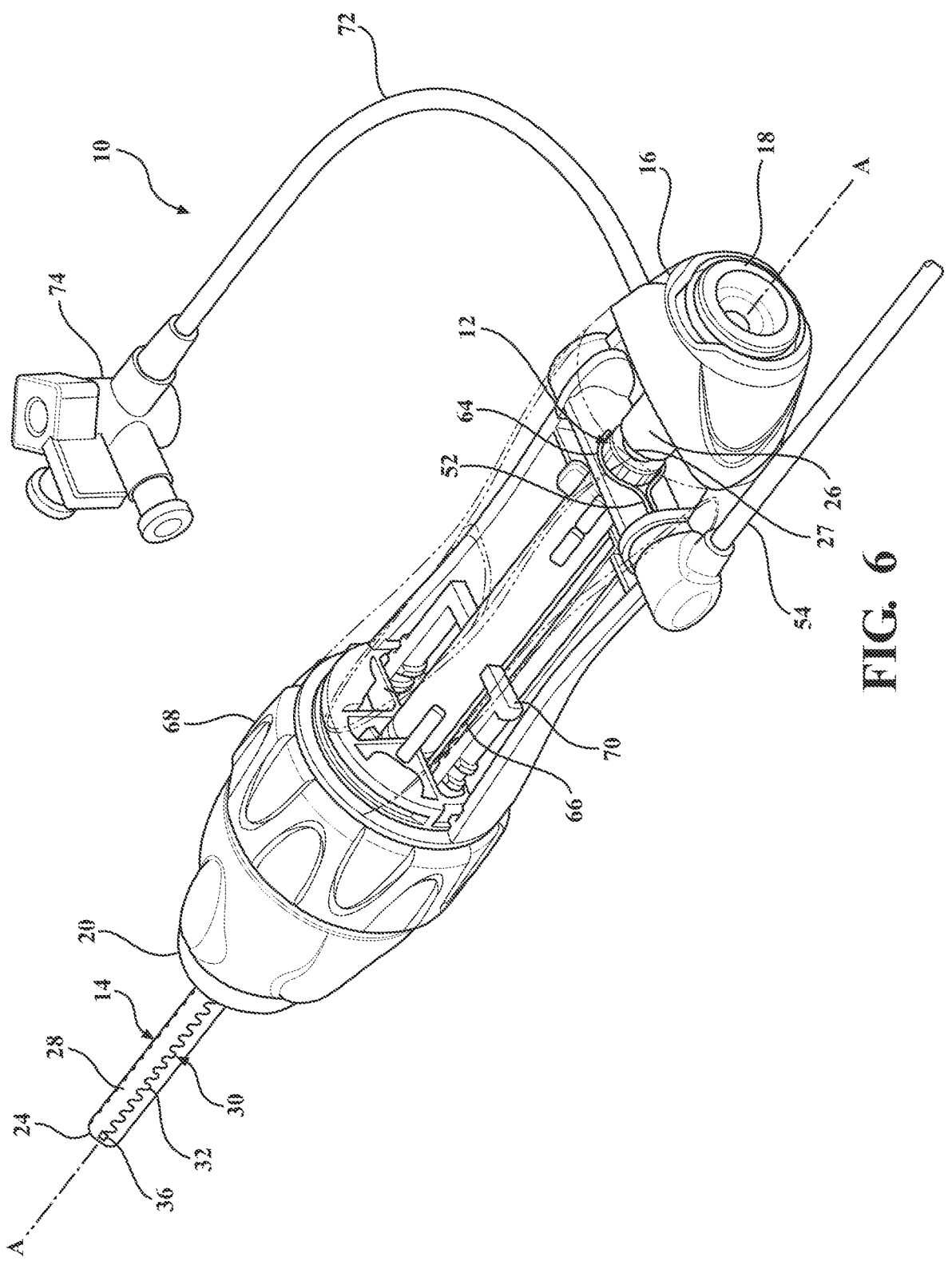
FIG. 6 is a perspective view of the handle assembly constructed in accordance with a second aspect and illustrating a portion of the handle in phantom lines to illustrate the ring connector integrated into a cord inner support of the housing.
Figure 8:
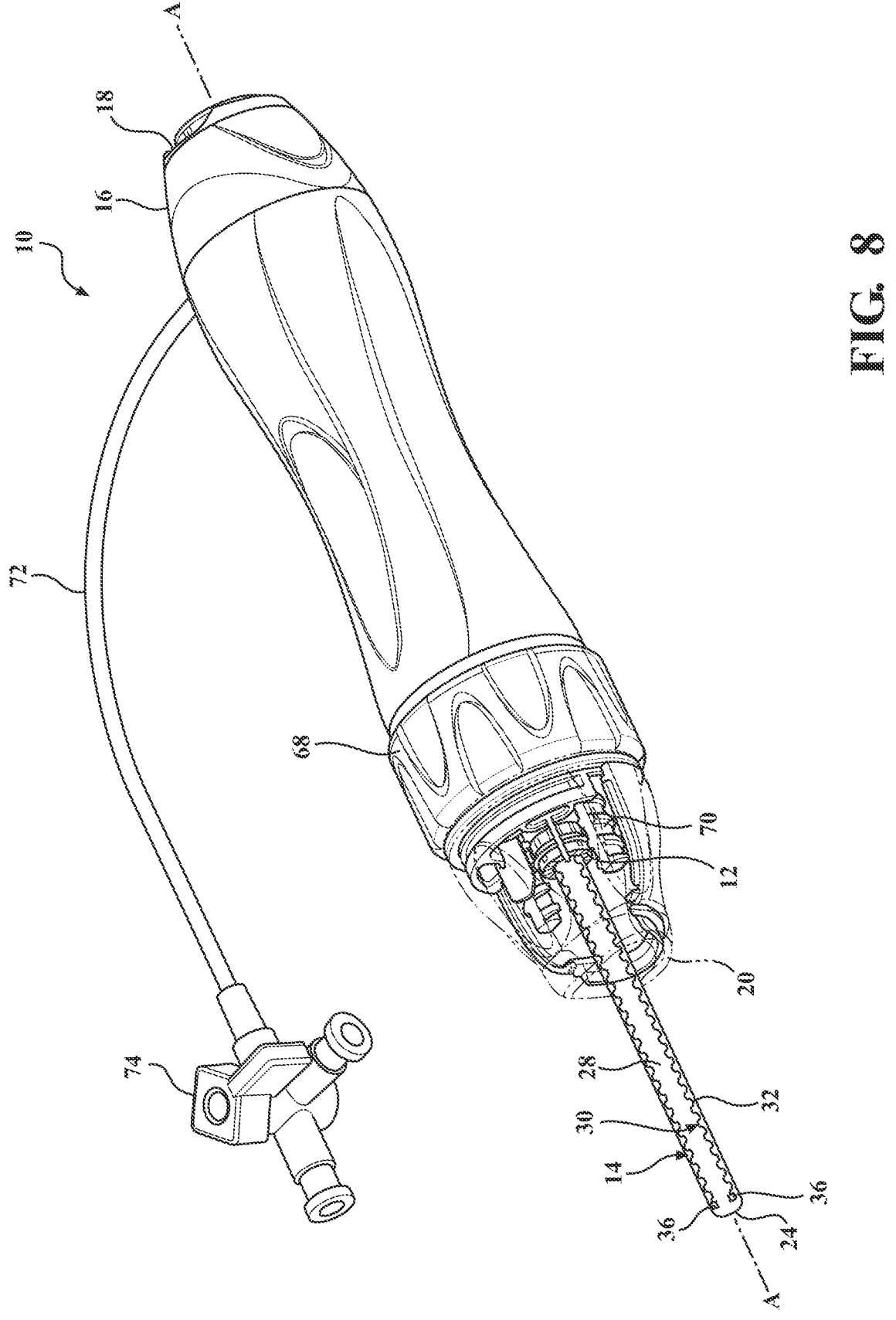
FIG. 8 is a perspective view of the handle assembly in accordance with a third aspect and illustrating a distal end of the housing in phantom lines to illustrate the ring connector co-axially aligned with the smart catheter adjacent the distal end of the housing.

Referring to the Figures, wherein like numerals indicate corresponding parts throughout the several views, the handle assembly 10 is generally illustrated in FIGS. 3, 6 and 8. The handle assembly 10 includes a housing 16 extending along an axis A from a proximal end 18 to a distal end 20. A smart catheter 14 extends through the housing 16 along the axis A from a receiving end 22 disposed adjacent the proximal end 18 to a distal tip 24 that extends outwardly from and terminates in spaced relationship with the distal end 20 of the housing 16. A valve assembly 26 is disposed adjacent to the proximal end 18 of the housing 16 and in sealed fluid communication with the receiving end 22 of the smart catheter 14 at a distal valve end 27 for allowing a medical device to be received and passed through the smart catheter 14 and towards the distal tip 24 for use during a medical procedure on a patient. An example of the valve assembly 26 is disclosed in Applicant's U.S. Pat. No. 9,884,175, the disclosure of which is incorporated herein by reference. However, other valve assemblies may be used without departing from the scope of the subject disclosure.

The smart catheter 14 includes an outer catheter surface 28 extending annularly about the axis A between the receiving end 22 and the distal tip 24 to define an outer diameter $D_o$ for the smart catheter 14. At least one circuit 30 is disposed on the outer catheter surface 28 and includes a circuit trace 32 extending between a proximal contact pad 34 disposed adjacent the receiving end 22 of the smart catheter 14 and a distal circuit end a disposed adjacent the distal tip 24 of the smart catheter 14. In a preferred arrangement, the at least one circuit 30 extends to a distal contact pad 36 at the distal circuit end for being disposed in electrical communication with at least one working component (such as a sensor) during use of the handle assembly 10. However, this sensor working component could also be incorporated into the at least one circuit 30 at the distal circuit end, such that a distal contact pad 36 may not be required. In either arrangement, the at least one circuit 30 is preferably comprised of copper due to its low cost and high conductivity, but other conductive materials could be utilized without departing from the scope of the subject disclosure. As best illustrated in FIGS. 1, 3, 6 and 8, in a preferred arrangement the at least one circuit 30 includes a plurality of circuits 30 extending along the outer catheter surface 28 each disposed in circumferentially spaced relationship with one another and extending between respective proximal and distal contact pads 34, 36. Further, although the circuit trace 32 is shown wide and the proximal and distal contact pads 34, 36 are shown as being large, each could be designed on a smaller scale than illustrated in the Figures. If a plurality of circuits 30 are included, the proximal and distal contact pads 34, 36 could be offset relative to one another to support a plethora of electrical connections, as will be appreciated in view of the following disclosure.

A ring connector 12 is coaxially aligned with the smart catheter 14 in radially surrounding relationship with a portion of the outer catheter surface 28 to dispose the ring connector 12 in electrical communication with the at least one circuit 30. More specifically, the ring connector 12 includes an annular body 38 presenting an outer connector surface 40 and an inner connector surface 42 each extending circumferentially around the axis A in radially spaced relationship with one another. The inner connector surface 42 defines a central opening 44 having an inner diameter $D_i$ being approximately equal to the outer diameter $D_o$ of the outer catheter surface 28 for disposing the inner connector and outer catheter surfaces 28, 42 in opposing and direct contact with one another when the smart catheter 14 is inserted and passed through the ring connector 12 during manufacture of the handle assembly 10. The ring connector 12 also includes at least one electrical connector 46 comprised of conductive metal that extends along at least the inner connector surface 42 and is disposed in abutting and electrical communication with the proximal contact pad 34 of the circuit 30 for establishing the electrical connection between the ring connector 12 and the smart catheter 14. In a preferred arrangement, the at least one electrical connector 46 includes a plurality of electrical connectors 46 arranged around the inner connector surface 42 of the annular body 38 in circumferentially spaced relationship with one another, each disposed in abutting and electrical connection with a proximal contact pad 34 of a respective one of the plurality of circuits 30. Although the preferred arrangement is described in relation to an electrical connection between the electrical connector 46 and the proximal contact pad 34, the electrical connector 46 could also be disposed in abutting and electrical communication with other portions of the circuit 30, such as the circuit trace 32, without departing from the scope of the subject disclosure. In a preferred arrangement, the annular body 38 is a single, unitary component. However, the annular body 38 could also be comprised of multiple pieces (e.g., two semi-circular components which are joined together) without departing from the scope of the subject disclosure.

As briefly mentioned above, during manufacture of the handle assembly 10, the smart catheter 14 is inserted or passed through the ring connector 12 to dispose the inner connector surface 42 of the ring connector 12 in overlaying relationship with a portion of the outer catheter surface 28, preferably the portion including the proximal contact pad 34, as a result of the equally sized diameters $D_i$, $D_o$ of the inner connector surface 42 and the outer catheter surface 28. The sliding movement of the smart catheter 14 proximally and distally relative to the ring connector 12 provides for easy location and placement of the inner connector surface 42 of the ring connector 12 in radially surrounding and overlaying relationship with the portion of the outer catheter surface 28 including the proximal contact pad(s) 34 to dispose the at least one electrical connector 46 in electrical communication with the proximal contact pad(s) 34. Thus, the ring connector 12 simplifies the process of establishing an electrical connection with the at least one circuit 30 of the smart catheter 14 by eliminating the small, fragile wires and associated soldering and/or welding processes required by the prior art handle assemblies to establish an electrical connection with the circuit(s) 30 of the smart catheter 14. Put another way, in this simpler manufacturing design, the ring connector 12 functions as a female connector component and the circuit 30, preferably the proximal contact pads 34, arranged on the outer catheter surface 28 functions as the male connector component to establish a solderless electrical connection between the ring connector 12 and the smart catheter 14. Thus, the resultant handle assembly 10 is not only more cost effective and easier to assemble due to the solderless design, but the ring connector 12 also makes the overall handle assembly 10 more robust due to reduced likelihood of connector breakage. The ring connector 12 also provides for increased yields for catheter assembly lines that have electrodes/electrical connections from the smart catheter to the handle assembly.

Figure 1:
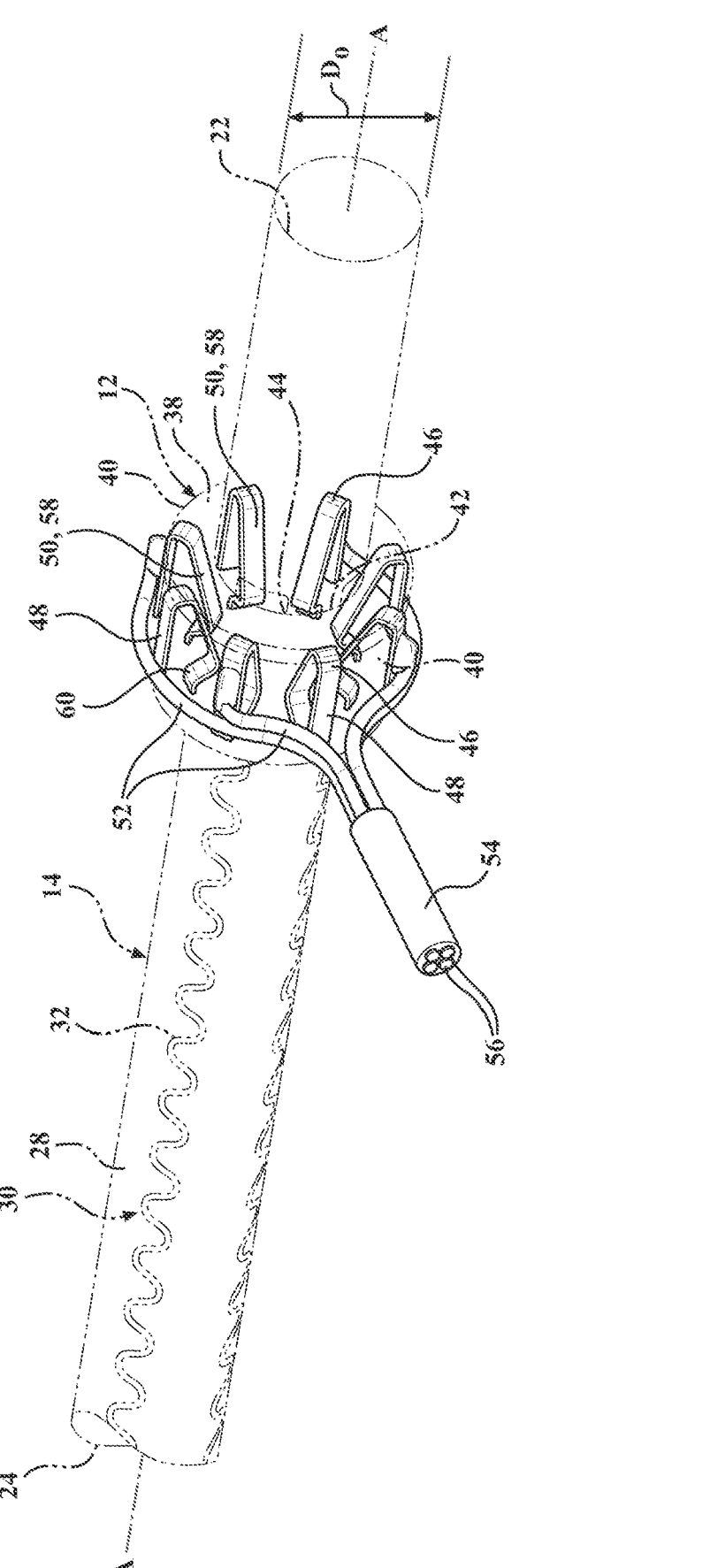
FIG. 1 is a perspective view of a smart catheter including a plurality of circuits extending along an outer catheter surface and a ring connector co-axially aligned with the smart catheter and disposed in radially surrounding relationship with a portion of the outer catheter surface to dispose the ring connector in electrical connection with the plurality of circuits.
Figure 2:
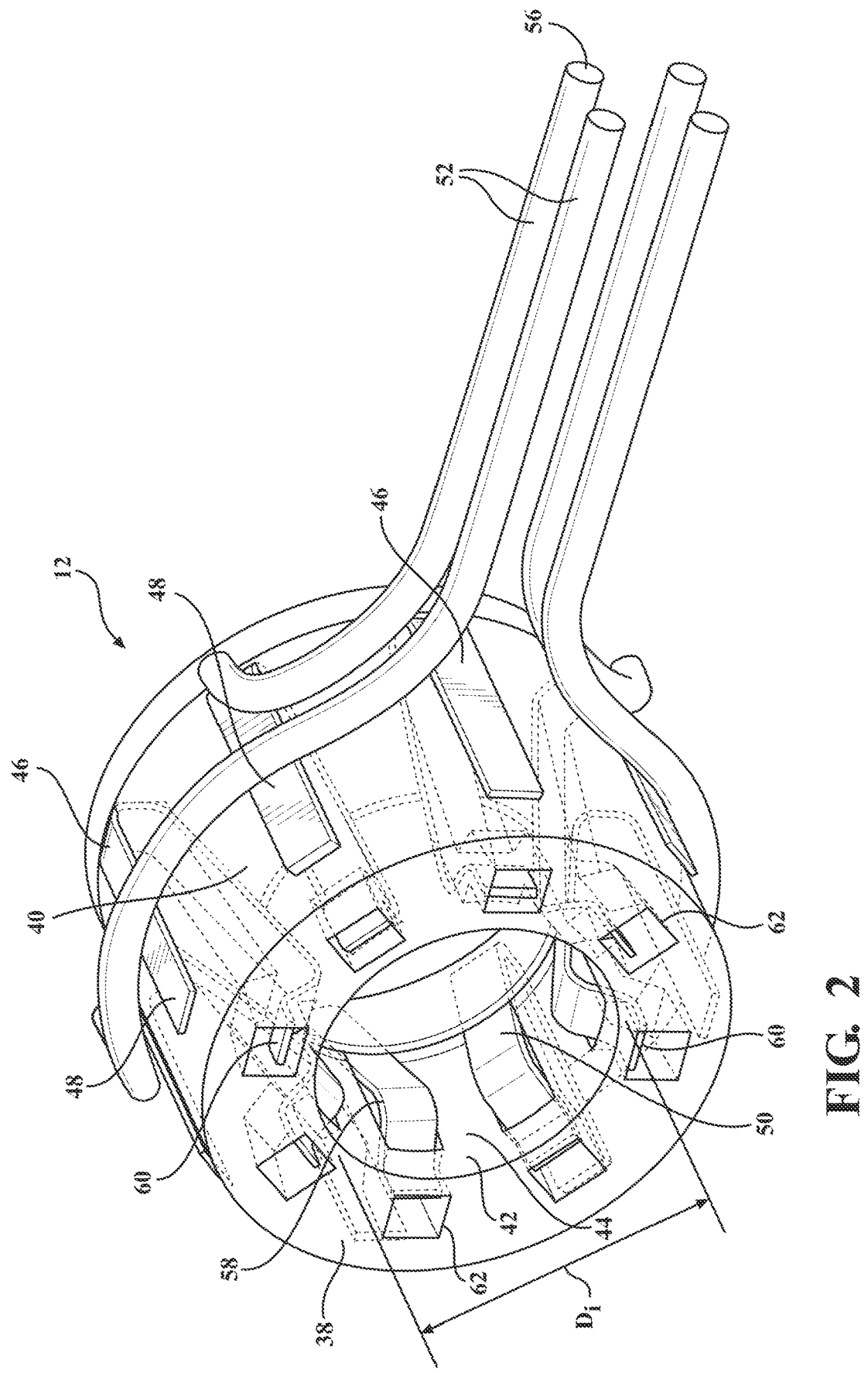
FIG. 2 is a perspective view of the ring connector illustrating an annular body presenting an inner connector surface defining a central opening having an inner diameter $D_i$ and a plurality of electrical connectors disposed in circumferentially spaced relationship with one another and each extending through the annular body from an outer electrical connecting portion disposed along an outer connector surface of the annular body to an inner electrical connecting portion disposed along the inner connector surface.
Figure 4:
FIG. 4 is a magnified view of the ring connector and the valve assembly more clearly illustrating the ring connector disposed in spaced and adjacent relationship with a distal valve end of the valve assembly and the inner electrical connecting portion of the electrical connector disposed in abutting relationship with a proximal contact pad of the circuit.

As best illustrated in FIGS. 1-2 and 4, each of the plurality of electrical connectors 46 extends through the annular body 38 from an outer electrical connecting portion 48 disposed along the outer connector surface 40 to an inner electrical connecting portion 50 disposed along the inner connector surface 42 and in abutting and electrical communication with a respective one of the proximal contact pads 34 of the plurality of circuits 30. A plurality of electrical wires 52 are each electrically connected, such as via soldering, to a respective one of the second electrical connecting portions 50 and extend collectively outwardly from the housing 16 as a wire bundle passing through a sheath 54 (See FIG. 1) to respective wire ends 56 for connection to an external controller (not expressly shown) or the like disposed in an environment of the handle assembly 10 for ultimately receiving feedback from and controlling the at least one working catheter component via the electrically interconnected circuit 30 and ring connector 12. The ring connector 12 provides a simplified electrical connection of the controller to the smart catheter 14 from an environment of the handle assembly 10, by allowing umbilical wire connectors or the like to be connected to the exposed wire end(s) 56 on the outside of the housing 16, either before the handle assembly 10 is manufactured, such that the ring connector 12 can be slipped over the smart catheter 14 as a complete unit, or alternatively after manufacture of the handle assembly 10.

As best illustrated in FIGS. 1-2 and 4, in a preferred arrangement the at least one electrical connector 46 is a "springform" component in which the inner electrical connecting portion 50 includes a spring component 58 that extends radially inwardly from the inner connector surface 42 and is self-biased towards the axis A such that it will resist radially outward movement. The inner electrical connecting portion 50 also includes a leg component 60 that is connected to the spring component 58 and is seated within a chamber 62 defined by the annular body 38. When the smart catheter 14 is inserted into and passed through the central opening 44 of the ring connector 14, the outer catheter surface 28 is disposed in abutting relationship with the spring component 58 and pushes the spring component 58 towards the inner connector surface 42, during which the leg component 60 correspondingly travels within the chamber 62 radially outwardly from adjacent the inner connector surface 42 to adjacent the outer connector surface 40. Once the ring connector 12 is arranged in coaxially aligned relationship with the smart catheter 14 around the portion of the outer catheter surface 28 having the proximal contact pads 34, the resistive force of the spring component 58 advantageously maintains contact with the proximal contact pads 34 to ensure an electrical connection during use of the handle assembly 10. Although the at least one electrical connector 46 is illustrated and described as a "springform" component, the inner connector surface 42 could also be arranged as a spring-loaded POGO pin without departing from the scope of the subject disclosure.

The annular body 38 of the ring connector 12 is comprised of a non-conductive material, preferably plastic, to provide electric isolation/insulation for the electrical connectors 46. The annular body 38 is also preferably a molded or machined component that could consist of two or more molded/machined components fixed together or as one single molded component (with insert-molded electrical connectors 46) such that the mounted electrical connectors 46 are fixed in position.

Figure 5:
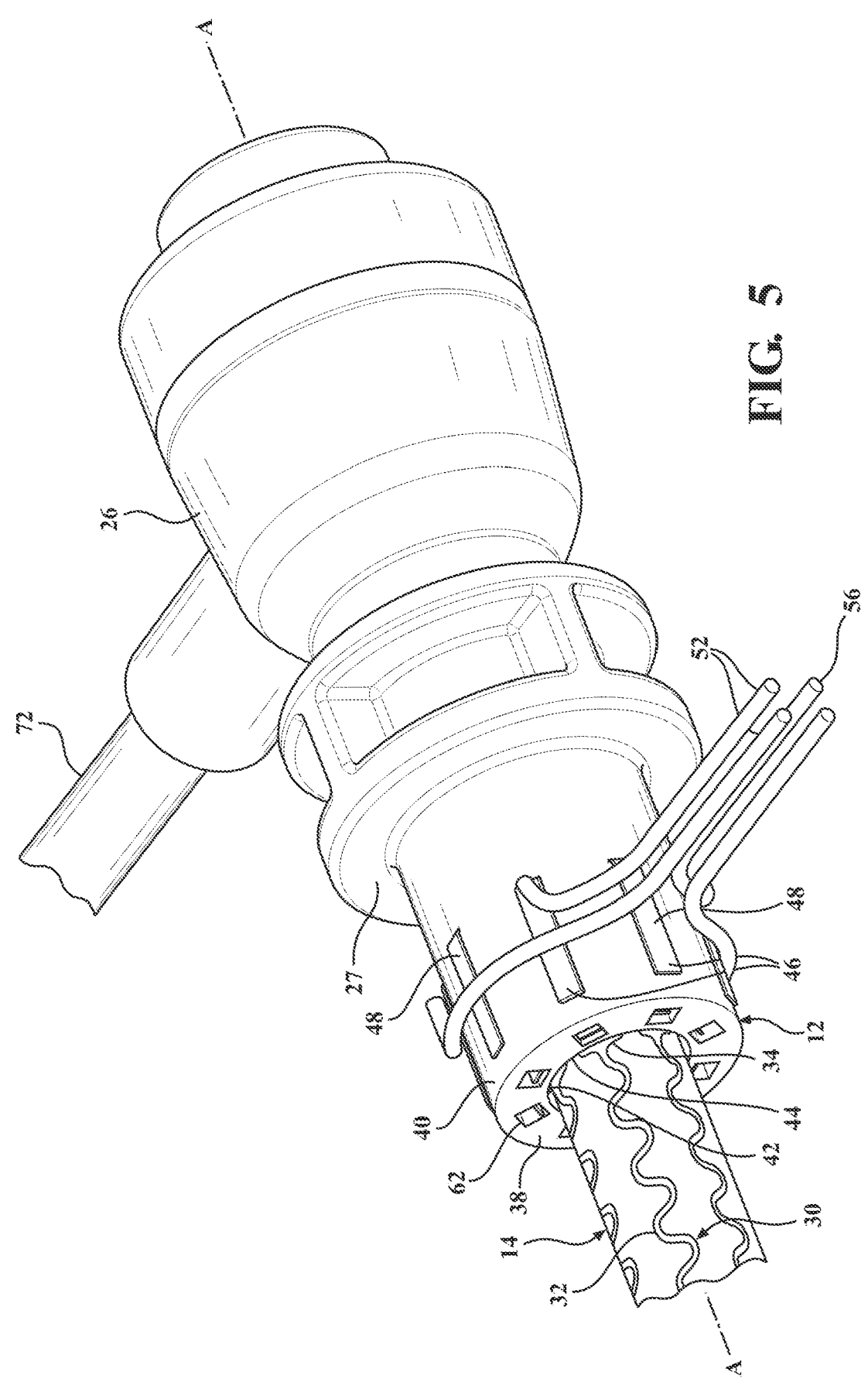
FIG. 5 is a magnified view of the ring connector and the valve assembly in an alternative arrangement in which the ring connector is an integral component of the valve assembly adjacent the distal valve end.
Figure 7:
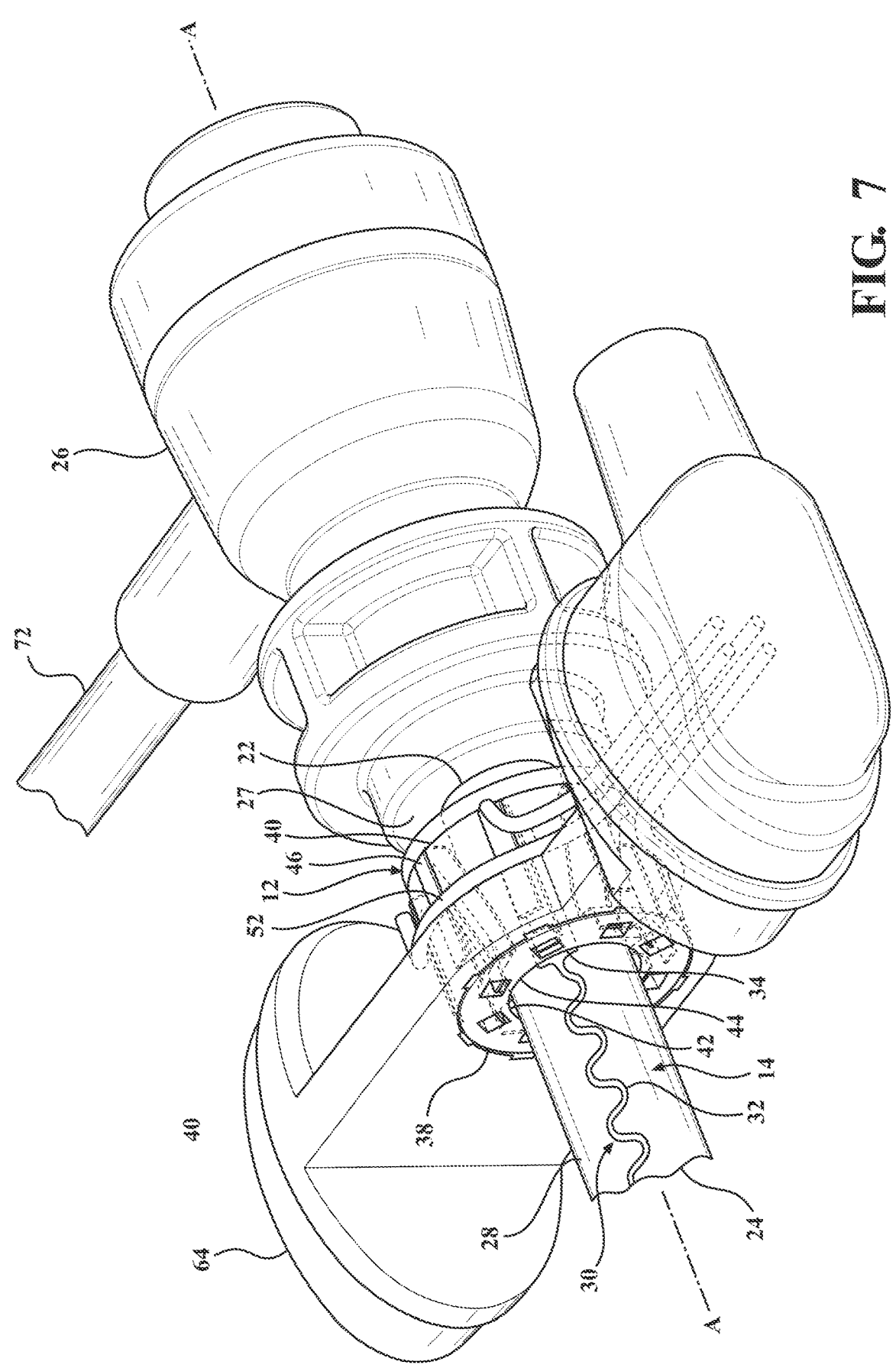
FIG. 7 is a magnified view of the ring connector and the cord inner support in the second aspect of the handle assembly.

As best illustrated in FIGS. 3, 6 and 8, the ring connector 12 could be arranged at various locations within the handle assembly 10 to provide flexibility with regard to proximal and distal placement of the ring connector 12 relative to the smart catheter 14. For example, as best illustrated in FIGS. 3 and 5, the ring connector 12 can be an integral component to components disposed inside of the handle assembly 10, such as an integral component of the valve assembly 26 secured to the distal valve end 27 adjacent the proximal end 18 of the housing 16. Alternatively, as best illustrated in FIGS. 4 and 8, the ring connector 12 could be a separate, stand-alone component disposed either adjacent the distal valve end 27 of the valve assembly 26 (FIG. 4) or adjacent the distal end 20 of the housing 16 (FIG. 8). In still yet an alternative arrangement, and as best illustrated in FIGS. 6-7, the ring component 12 could be an integral component of the housing 16, such as an integral component of a cord inner support 64 extending through the housing 16 transverse to the axis A and disposed adjacent the distal valve end 27 of the valve assembly 26. Although not expressly illustrated, the ring connector 12 could also be co-axially aligned with the smart catheter 14 outside of the housing 16, without departing from the scope of the subject disclosure. In any arrangement, the quick and easy electrical connection between the ring connector 12 and the smart catheter 14 is maintained.

Consistent with handle assemblies for steerable catheters, such as disclosed in Applicant's U.S. Pat. No. 9,737,688, the smart catheter 14 includes at least one deflection wire 66 that extends from the distal tip 24 and into the housing 16 for use in curling the distal tip 24 in response to movement of the at least one deflection wire 66. The handle assembly 10 includes a dial 68 rotatably connected to the housing 16 for rotation about the axis A by a user, and at least one actuation screw shaft 70 is disposed within the housing 16 and connected with the at least one deflection wire 66. The dial 68 and actuation screw shaft 70 are operably connected with one another such that rotation of the dial 68 by the user effectuates axial movement of the actuation screw shaft 70 to provide for movement of the at least one deflection wire 66 to curl the steerable, smart catheter 14. As best illustrated in FIGS. 1, 3, and 6, the proximal end 18 of the housing also receives a hose 72 of a stopcock assembly 74 of the smart catheter 14.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A handle assembly for a smart catheter comprising:

a housing extending along an axis from a proximal end to a distal end;

a smart catheter extending through the housing and along the axis from a receiving end to a distal tip that extends outwardly from and terminates in spaced relationship with said distal end of said housing;

said smart catheter including an outer catheter surface having an outer diameter $D_o$ extending annularly about the axis between said receiving end and said distal tip;

at least one circuit disposed along said outer catheter surface and extending between said receiving end and said distal tip;

said at least one circuit including a circuit trace extending from a proximal contact pad disposed adjacent said receiving end to a distal circuit end disposed adjacent said distal tip;

a ring connector co-axially aligned with said smart catheter and disposed in radially surrounding relationship with a portion of said outer catheter surface;

said ring connector including an annular body presenting an outer connector surface and an inner connector surface each extending circumferentially about the axis in radially spaced relationship with one another;

said inner connector surface defining a central opening having an inner diameter $D_i$ being approximately equal to said outer diameter $D_o$ of said outer catheter surface for disposing said inner connector and outer catheter surfaces in contact with one another when said ring connector is co-axially aligned with said ring connector;

said inner connector surface of said ring connector including at least one electrical connector, and said ring connector disposed in radially surrounding relationship with said at least one proximal contact pad to dispose said at least one electrical connector in abutting and electrical connection with said at least one proximal pad and establish electrical communication between said ring connector and said at least one circuit.

2. The handle assembly as set forth in claim 1, further comprising:

said smart catheter including a plurality of circuits each extending in circumferentially spaced relationship with one another between respective proximal contact pads and distal circuit ends;

said at least one electrical connector including a plurality of electrical connectors arranged around said inner connector surface in circumferentially spaced relationship with one another and each disposed in abutting and electrical communication with a respective one of said plurality of contact pads;

each of said plurality of electrical connectors extending through said annular body from an outer electrical connecting portion disposed along said outer connector surface to an inner electrical connecting portion disposed along said inner connector surface and in abutting relationship with a respective one of said plurality of proximal contact pads; and a plurality of electrical wires each electrically connected to a respective one of said outer electrical connecting portions and extending outwardly from said housing to respective wire ends disposed in an environment of the handle assembly for connection to an external controller.

3. The handle assembly as set forth in claim 2, wherein said plurality of electrical wires extend collectively outwardly from said housing as a wire bundle passing through a sheath.

4. The handle assembly as set forth in claim 2, wherein each of said inner electrical connecting portions includes a spring component extending radially inwardly from said inner connector surface and self-biased towards said axis to resist radially outward movement for maintaining contact between said inner electrical connection portions and said proximal contact pads.

5. The handle assembly as forth in claim 4, wherein each of said inner electrical connecting portions include a leg component connected with said spring component and seated within a chamber defined by said annular body for traveling within said chamber from adjacent said inner connector surface towards said outer connector surface during contact of said spring component with said proximal contact pad.

6. The handle assembly as set forth in claim 2, further comprising:

a valve assembly disposed adjacent said proximal end of said housing and in fluid communication with said receiving end of said smart catheter; and said connector ring integrally formed with a distal valve end of said valve assembly.

7. The handle assembly as set forth in claim 2, further comprising;

a valve assembly disposed adjacent said proximal end of said housing and in fluid communication with said receiving end of said smart catheter; and said connector ring disposed in spaced and adjacent relationship with a distal valve end of said valve assembly.

8. The handle assembly as set forth in claim 2, wherein said ring connector is integrally formed with a cord inner support extending through said housing transverse to said axis.

9. The handle assembly as set forth in claim 2, wherein said connector ring is disposed adjacent said distal end of said housing.

10. The handle assembly as set forth in claim 1, wherein said annular body is comprised of a non-conductive material to provide electrical isolation for said at least one electrical connector.

11. A handle assembly for a smart catheter comprising:

a housing extending along an axis from a proximal end to a distal end;

a smart catheter extending through the housing and along the axis from a receiving end to a distal tip that extends outwardly from and terminates in spaced relationship with said distal end of said housing;

said smart catheter including an outer catheter surface having an outer diameter $D_o$ extending annularly about the axis between said receiving end and said distal tip;

a ring connector co-axially aligned with said smart catheter and disposed in radially surrounding relationship with a portion of said outer catheter surface;

said ring connector including an annular body presenting an outer connector surface and an inner connector surface each extending circumferentially about the axis in radially spaced relationship with one another;

said inner connector surface defining a central opening having an inner diameter $D_i$ being approximately equal to said outer diameter $D_o$ of said outer catheter surface for disposing said inner connector and outer catheter surfaces in contact with one another when said ring connector is co-axially aligned with said ring connector;

said smart catheter including a plurality of circuits each extending in circumferentially spaced relationship with one another between respective proximal circuit ends and distal circuit ends, and said ring connector including a plurality of electrical connectors arranged around said inner connector surface in circumferentially spaced relationship with one another and each disposed in abutting and electrical communication with a respective one of said plurality of circuits.

12. The handle assembly as set forth in claim 11, further comprising:

each of said plurality of electrical connectors extending through said annular body from an outer electrical connecting portion disposed along said outer connector surface to an inner electrical connecting portion disposed along said inner connector surface and in abutting relationship with a respective one of said plurality of circuits; and a plurality of electrical wires each electrically connected to a respective one of said outer electrical connecting portions and extending outwardly from said housing to respective wire ends disposed in an environment of the handle assembly for connection to an external controller.

13. The handle assembly as set forth in claim 12, wherein said plurality of electrical wires extend collectively outwardly from said housing as a wire bundle passing through a sheath.

14. The handle assembly as set forth in claim 12, wherein each of said inner electrical connecting portions includes a spring component extending radially inwardly from said inner connector surface and self-biased towards said axis to resist radially outward movement for maintaining contact between said plurality of electrical connectors and a respective one of said plurality of circuits.

15. The handle assembly as forth in claim 14, wherein each of said inner electrical connecting portions include a leg component connected with said spring component and seated within a chamber defined by said annular body for traveling within said chamber from adjacent said inner connector surface towards said outer connector surface during contact of said spring component with a respective one of said plurality of circuits.

16. The handle assembly as set forth in claim 12, wherein said ring connector is integrally formed with a cord inner support extending through said housing transverse to said axis.

17. The handle assembly as set forth in claim 11, wherein said annular body is comprised of a non-conductive material to provide electrical isolation for said plurality of electrical connectors.

18. A method of assembling a handle assembly for a smart catheter, the method comprising:

providing a housing extending along an axis from a proximal end to a distal end;

disposing a ring connector within said housing in axially aligned relationship with the axis, the ring connector including an annular body presenting an inner connector surface defining a central opening having an inner diameter $D_i$, and the inner connector surface including at least one electrical connector;

inserting a smart catheter into the housing, the smart catheter including an outer catheter surface having an outer diameter $D_o$ being approximately equal to the inner diameter $D_i$ of the central opening and at least one circuit including a circuit trace extending from a proximal contact pad disposed adjacent a receiving end of the smart catheter to a distal circuit end disposed adjacent a distal tip of the smart catheter; and passing the smart catheter through the ring connector to dispose the inner connector surface of the ring connector in contact and radially surrounding relationship with a portion of the outer catheter surface of the smart catheter and the at least one electrical connector in abutting and electrical communication with the at least one proximal pad.

19. The method as set forth in claim 18, wherein the at least one electrical connector includes a spring component extending radially inwardly from the inner connector surface and self-biased towards the axis to resist radially outward movement, and said step of passing the smart catheter through the ring connector includes disposing the outer catheter surface in abutting relationship with the spring component to push the spring component radially outwardly and establish a resistive force of the spring component which maintains electrical contact between the at least one electrical connector and the at least one proximal contact pad.

20. The method as set forth in claim 19, wherein the at least one electrical connector includes a leg component connected with the spring component and seated within a chamber defined by the annular body, and said step of passing the smart catheter through the ring connector includes pushing the leg component radially outwardly during commensurate movement of the spring component.

* * * * *